United States Patent
Rodiera Olive

Patent Number: 5,957,860
Date of Patent: Sep. 28, 1999

[54] METHOD AND APPARATUS FOR MONITORING AND/OR CONTROLLING THE NEUROMUSCULAR BLOCKING, SPECIALLY THE BLOCKING PRODUCED BY MUSCULAR RELAXING PHARMACEUTICALS DURING ANAESTHESIA

[76] Inventor: Jose J Rodiera Olive, Calle Teodora Lamadrid, 52-60 E-08 022, Barcelona, Spain

[21] Appl. No.: 08/817,336
[22] PCT Filed: Jul. 30, 1996
[86] PCT No.: PCT/ES96/00156
§ 371 Date: May 23, 1997
§ 102(e) Date: May 23, 1997
[87] PCT Pub. No.: WO97/05923
PCT Pub. Date: Feb. 20, 1997

[30] Foreign Application Priority Data
Aug. 4, 1995 [ES] Spain ................... 9501591

[51] Int. Cl.⁶ .................................. A61B 5/00
[52] U.S. Cl. .................. 600/546; 600/547; 600/554
[58] Field of Search .................. 600/384, 386, 600/393, 491, 499, 546, 547, 591, 554

[56] References Cited

U.S. PATENT DOCUMENTS

| | | | |
|---|---|---|---|
| 3,898,983 | 8/1975 | Elam | 128/2 N |
| 4,088,133 | 5/1978 | Twentier | 128/303.13 |
| 4,291,705 | 9/1981 | Severinghaus et al. | 128/733 |
| 4,432,368 | 2/1984 | Russek | 128/644 |
| 4,848,359 | 7/1989 | Bournonville | 128/741 |
| 5,016,635 | 5/1991 | Graupe | 128/421 |
| 5,061,234 | 10/1991 | Chaney | 600/14 |
| 5,092,344 | 3/1992 | Lee | 128/741 |
| 5,131,401 | 7/1992 | Westenskow et al. | 128/741 |
| 5,256,156 | 10/1993 | Kern et al. | 604/246 |
| 5,304,206 | 4/1994 | Baker, Jr. et al. | 602/2 |
| 5,327,902 | 7/1994 | Lemmen | 128/734 |
| 5,333,618 | 8/1994 | Lekhtman et al. | 128/734 |
| 5,354,320 | 10/1994 | Schaldach et al. | 607/46 |
| 5,368,042 | 11/1994 | O'Neal et al. | 128/733 |
| 5,374,283 | 12/1994 | Flick | 607/46 |
| 5,397,338 | 3/1995 | Grey et al. | 607/115 |
| 5,443,494 | 8/1995 | Paolizzi et al. | 607/149 |
| 5,540,235 | 7/1996 | Wilson | 128/741 |

FOREIGN PATENT DOCUMENTS

| | | |
|---|---|---|
| 0436121A1 | 11/1990 | European Pat. Off. |
| 1359777 | 3/1964 | France. |
| 2 551 965 | 12/1985 | France. |
| 1586 12 | 8/1981 | Germany. |
| WO92/22250 | 12/1992 | WIPO. |
| WO95/10323 | 4/1995 | WIPO. |

*Primary Examiner*—Max Hindenburg
*Attorney, Agent, or Firm*—Michael Best & Friedrich LLP

[57] ABSTRACT

The method consists in the stimulation of a nerve and the detection and measurement of the response and is characterized in that the nerve stimulation is done in the skin which covers the muscles on which the detection of the response is performed.

The apparatus comprises means for the application of the nerve stimulation, means for the detection of the response and, optionally, means for the monitoring of the neuromuscular block, and it is characterized in that said means are provided in a single body, which is a cuff of the type used for measuring arterial pressure, provided with means for a detection of pressure or connected to said means.

It is not necessary to stimulate any peripheral nerves, and the apparatus is more compact and handy.

18 Claims, 4 Drawing Sheets

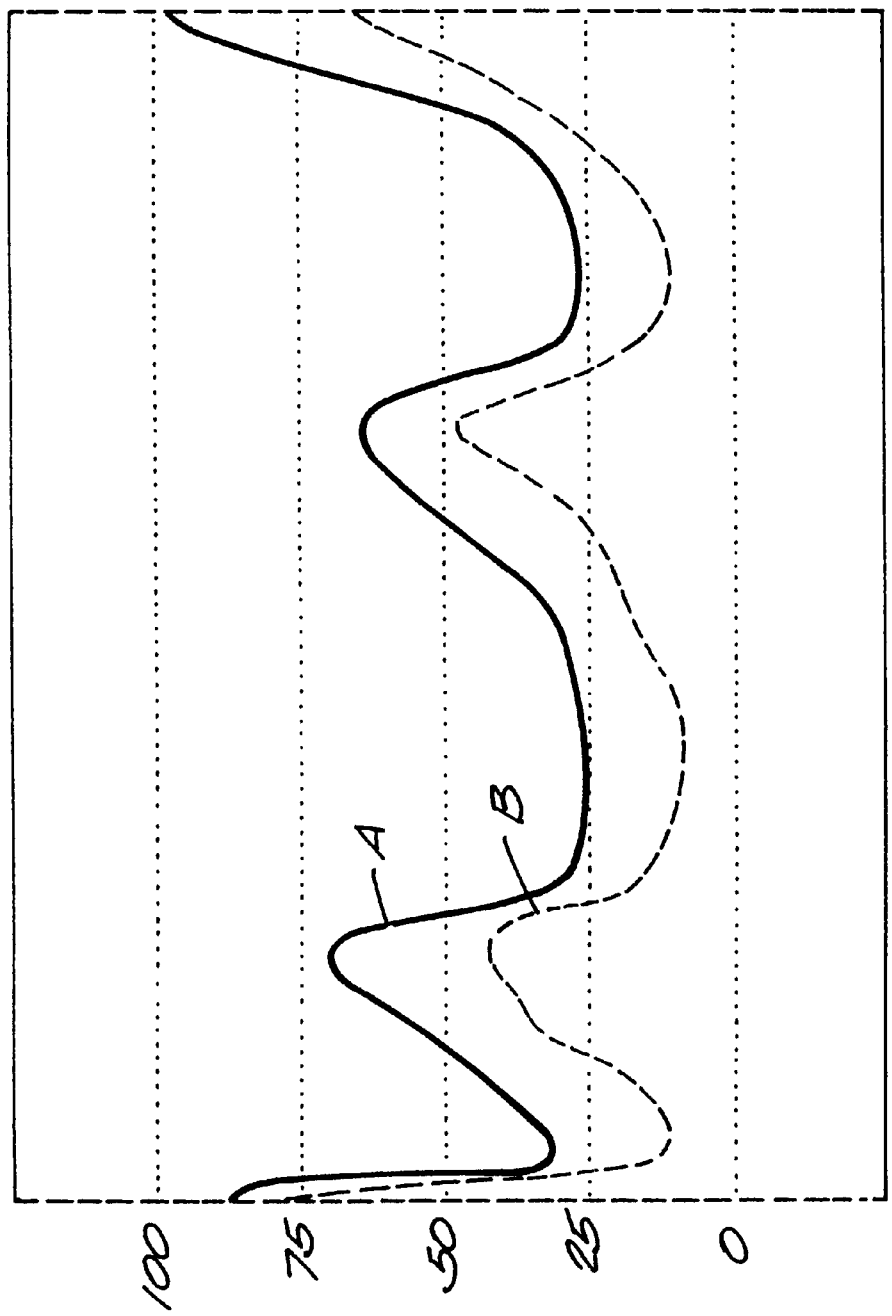

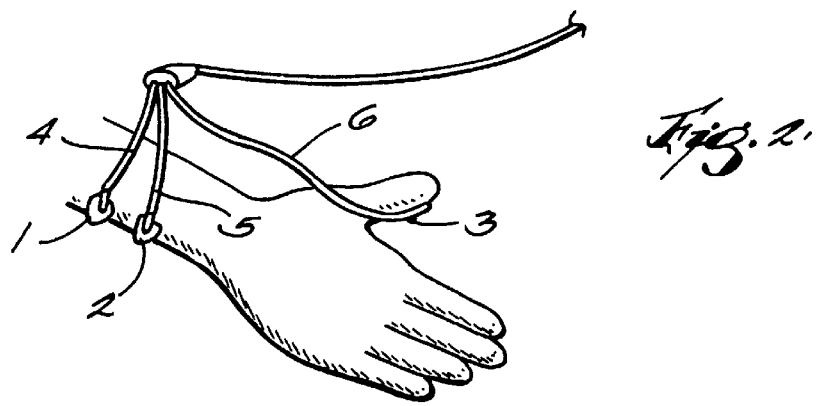
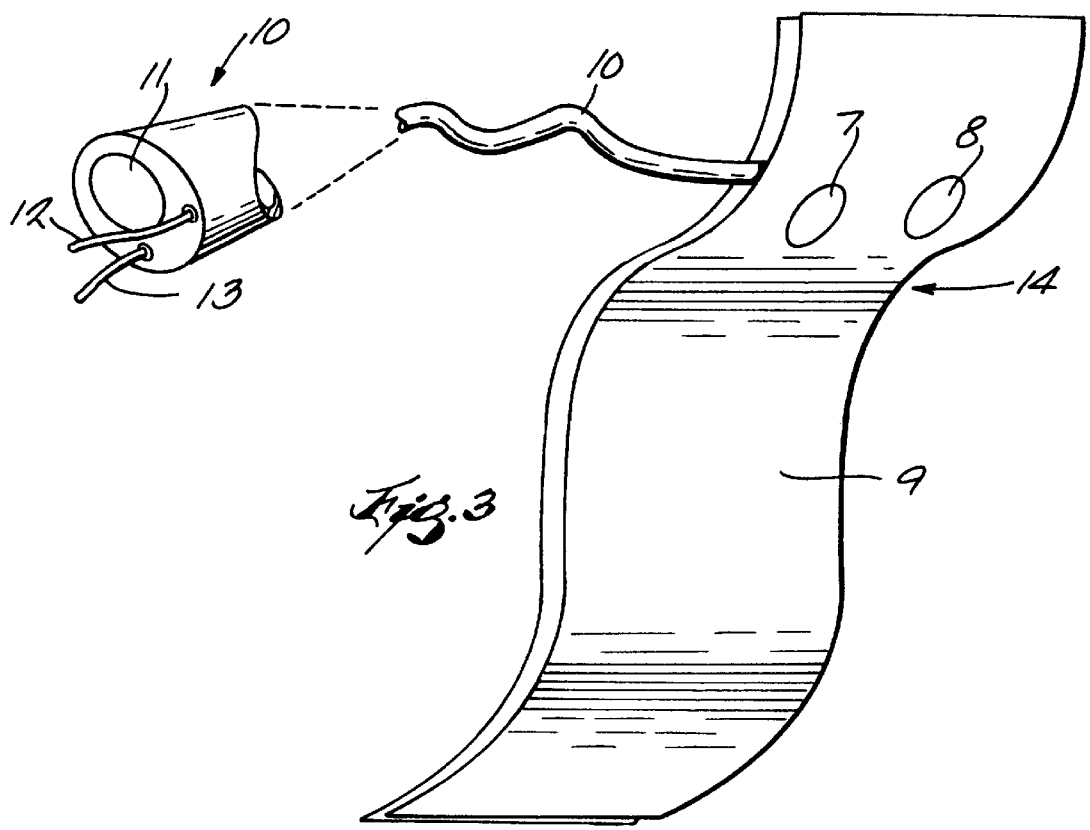

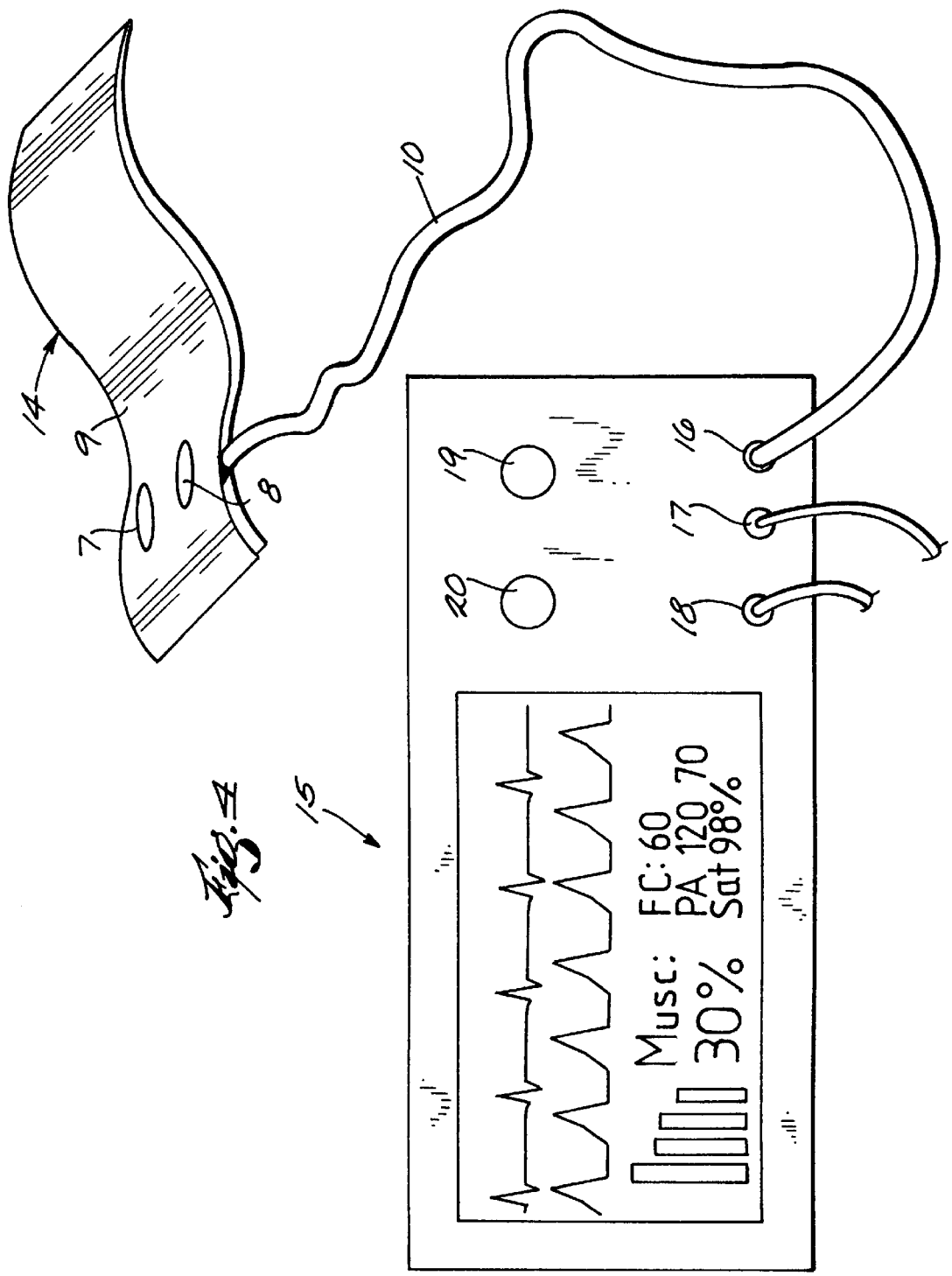

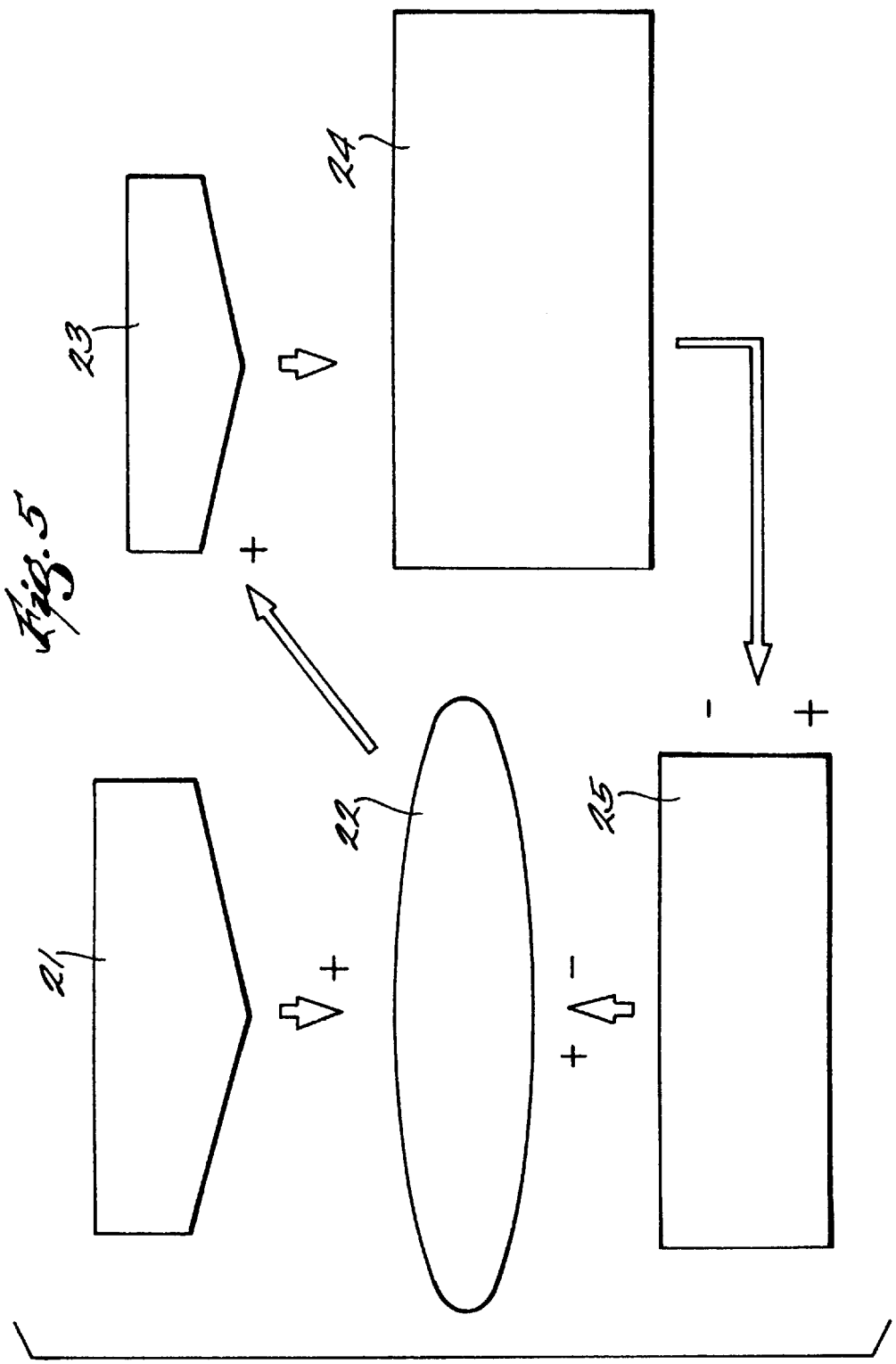

METHOD AND APPARATUS FOR MONITORING AND/OR CONTROLLING THE NEUROMUSCULAR BLOCKING, SPECIALLY THE BLOCKING PRODUCED BY MUSCULAR RELAXING PHARMACEUTICALS DURING ANAESTHESIA

The present invention pertains to a device for the monitoring and/or controlling of the neuromuscular block, especially that produced by muscle relaxant drugs used during anaesthesia.

Primarily, the new method and apparatus allow a quantification and control of the neuromuscular block by means of transcutaneous stimulation directly on the muscle, stimulating the intramuscular nerve pathways and the neural part of the motor plate without the need of having to stimulate a peripheral motor nerve.

The invention also allows a controlled administration of the blocker drug during the induction of the anaesthesia, as well as control of the neuromuscular block during the operation and control of the recovery when being awakened from the anaesthesia.

ANTECEDENTS OF THE INVENTION

It is known that major advances in surgery have come about from the application of muscle relaxant drugs during anaesthesia, which in addition to facilitating the work of the surgeon also allows a less traumatic intubation and facilitates mechanical respiration.

Likewise, muscle relaxation allows improved mechanical ventilation for intubated patients at intensive care wards.

It is also known that there are various factors which influence the duration and effect of the muscle relaxants, depending among other things on the body weight, the age, the physical condition and possible pathologies of the patient to whom this type of drug is being administered. In the event that the dose is insufficient, the intubation and the subsequent surgery might become more difficult; in the case of overdosage, the patient upon awakening from the anaesthesia might present respiratory insufficiency and a need for prolonged artificial respiration, which would delay their leaving the operating theater or their admission to a special care ward.

Other dangers of overdosage or poor reversal of the effects of muscle relaxants might be serious complications such as aspiration of vomit on account of faulty reflexes or respiratory failure, which complications may eventually cause the death of the patient.

In order to avoid these complications, at present, the status of the neuromuscular block is evaluated by means of stimulation of a peripheral motor nerve and measurement of the degree of motility of the muscle innervated by said nerve.

There are various methods and devices designed to stimulate peripheral nerves by means of transcutaneous electrodes, for example, the stimulators of Neuro Technology, Inc., Houston, Tex., U.S.A. The most important problem lies in the evaluation or measurement and monitoring of the neuromuscular block and the adequate administration of the muscle relaxant drug to maintain the desired level of blockage. At present, the evaluation of the block is done by evaluation of the electrical activity, the force or the movement of the muscle during its contraction. The methods used up to the present date are:

1) The visual method. One visually evaluates the movement of a muscle after the stimulation of the motor nerve which innervates it. The inexactitude and difficulty of quantification of the method are obvious, but its simplicity makes it the one which is used most frequently today.

2) The tactile method. Similar to the preceding method, but in this case the evaluation is done by means of the perception through the hand of the anesthesiologist of the force of contraction of the patient after the stimulus. As in the preceding case, it is a subjective and inexact method, offering little guarantee of determining the exact degree of neuromuscular blockage.

3) By means of electromyography. This consists in the registration of the muscular electrical activity evoked by stimulating the motor nerve which innervates said muscle. There are various devices and apparatus on the market, which monitor the neuromuscular block by said technique, which is described, for example, in U.S. Pat. No. 4,291,705, among others. The primary problem which this technique entails is its difficulty of application and the sophistication of the equipment, so that it has only been used essentially in research, without coming to be used as a practical and routine technique.

4) By means of force transducers. In this case, one registers the force of the thumb when the ulnar nerve is stimulated. Again, there are various devices on the market, such as the "Relaxograph" of Biometer International A/S, Denmark. As in the preceding case, the primary problem consists in the complexity of the technique used, which involves having to immobilize the arm in order to perform a proper registration. For this reason, and the costly equipment, this device is not very practical for routine use.

5) By means of accelerometry. This method is, after the visual method, the most popular one. It is based on placing a biaxial or biaxial accelerometric sensor on the thumb which, when the ulnar nerve is stimulated, provokes a movement in same, which is picked up by the accelerometer. This is a rather valid method, but it still has the drawback that several electrodes separate from the sensor have to be put in place in order to stimulate the peripheral nerve. On the other hand, the accelerometer is fragile and requires a certain immobilization of the arm. Other placements of the accelerometer have been described, for example, on the face, in which case one must stimulate a motor branch of the facial nerve and the stimulus electrodes must arrive separately from the accelerometer, increasing the risk of certain of the elements becoming detached from the skin. As an example of monitors based on accelerometry, one can mention the "Accelograph" and "Tof-Guard" models, both of them from Biometer International A/S, Denmark, and that described in U.S. Pat. No. 4,817,628, which is another example of a facial accelerometer.

6) By means of flexible-sheet piezoelectric sensors. The phenomenon of piezoelectricity has been known for many years, as has been its application in the field of medicine, for example, with the application of piezoelectric sensors which, through their deformation, capture the plethysmographic wave transmitted to the skin. Based on this principle, the monitor of U.S. Pat. No. 5,131,401 requires, like the other methods, the stimulation of a peripheral motor nerve, primarily the ulnar nerve, and it comprises some cables for the stimulus electrodes and others for a sensor in the form of flexible piezoelectric sheets, which are placed on the palm of the hand and register the contraction of the muscles of the hand. Like the "Tof-Guard" model, it also has a microprocessor which, by means of a program, enables a programmed stimulation and visualization of the quantified response of the neuromuscular block.

The primary drawback presented by these monitors, except for the last one, is that they require the stimulation of a peripheral motor nerve, specifically the ulnar nerve, and the placement of the sensor on the hand or thumb. They likewise require the use of two electrodes for separate stimulation of the sensor element of the response, which increases the risk of a detachment of the electrodes or of the sensor.

Owing to this, the placement of the electrodes may be awkward and a certain immobilization of the limb is necessary, limiting the placement in other positions. On the other hand, this type of apparatus might be more sensitive to certain interference or involuntary movements of the patient.

With respect to the control of the neuromuscular block, there are various works based on pharmacokinetic models and short-circuit models, such as those described in individual articles of medical journals:

"Quantitative assessment of residual antidepolarizing block (Partil)" Ali H. H. et al., Br J Anaesthesia 1971 vol. 43 pp. 473–477.

"Monitoring of neuromuscular function" Ali H. H. et al., Anesthesiology 1976 vol. 45 pp. 216–249.

"A microcomputer based controller for neuromuscular block during surgery" Ritchie G. et al. Ann Biomed Eng 1985 vol. 13 pp. 3–15.

"Microcomputer based muscle relaxation monitor and controller for clinical use" Bradlow H. S. et al. Med Biol Eng Comput 1985, vol 23 pp. 547–555.

"Online parameter estimation and control of D-Tubocurarine-induced muscle relaxation." Rametti L. B. et al., Med Biol Eng Comput 1985 vol. 23 pp. 556–564.

"Online control of Atracurium induced muscle relaxation" Bradlow H. S. et al, J Biomed Eng 1986 vol. 8 pp. 772–775.

"Computer-Controlled Muscle Paralysis with atracurium in the Sheep" D. G. Lampard et al, Anesthesia and Intensive Care, vol. 41 (1986) pp. 316–320.

"Clinical automatic control of neuromuscular blockade" Asbury A. J. et al, Anaesthesia 1986 vol. 41 pp. 316–320.

"Infusion of vecuronium controlled by a closed-loop system" Br J Anaesth 1986 vol. 58 pp. 1100–1103.

"Closed-loop administration of Atracurium" N. R. Webster et al, Anesthesia vol. 42 (1987) pp. 1085–1091.

"A model-based self-adjusting two-phase controller for vecuronium-induced muscle relaxation during anaesthesia" Jalkist R. R., IEEE Transac Biomed Eng 1987 vol. 34 pp. 583–594.

"Closed-loop infusion of atracurium with four different anesthetic techniques" O'Hara D. A. et al, Anesthesiology 1991 vol 74 pp. 258–263.

These articles describe instances of control of the muscle relaxation by means of computers with pharmacokinetic models, through the previously mentioned sensors, or with closed-circuit systems.

There are correct approximations in all the instances, but even so they are still experimental and not very safe models, which owing primarily to the-need to stimulate a peripheral nerve are impractical and complicated in use, whether because of the type of transducer used or because of the pharmacokinetic model, which requires much data entry or very sophisticated computers.

DESCRIPTION OF THE INVENTION

The aforesaid drawbacks can be eliminated with the method and apparatus of the invention.

The method for monitoring and/or controlling the neuromuscular block which is the subject of the invention is characterized by the fact that the nerve stimulation is done on the skin covering the muscle or muscles on which the detection of the response to said stimulation is performed, that is, without having to stimulate any peripheral nerve.

Thanks to this method, it is not necessary to stimulate the peripheral nerve and the stimulator-detector device can be placed on the upper or lower limb, depending on the type of surgery being performed, without having to confine the stimulation to the ulnar nerve.

Optionally, the method of the invention also comprises the automatic control of the supply of the muscle relaxant drug on the basis of a detection of the muscle response.

The invention also pertains to an apparatus for the monitoring and/or controlling of the neuromuscular block, which comprises means for the application of the nerve stimulation, means for the detection of the response to the stimulation, and means for monitoring the neuromuscular block, and it is characterized by the fact that the means for the nerve stimulation and the means for the detection of the response are arranged in the same body.

Thanks to this arrangement in a single body, the following advantages are achieved:

i) a single element serves to measure the arterial pressure and to measure the neuromuscular block, achieving a more compact and handy device, ii) the placement becomes easier, iii) the independent disconnection of certain of the components is avoided, iv) it simplifies the monitoring in the operating theater.

According to another embodiment, the apparatus of the invention comprises means for the application of the nerve stimulation, means for the detection of the response to the stimulation, and means for the monitoring of the neuromuscular block, and it is characterized by the fact that it also comprises means for supply of the drug which produces the neuromuscular block and means of control which coordinate the generation of the stimulus, the registration of the activity, the data processing, the computation of the drug dosage and the control of the means for supply of the drug as a function of the computed dosage.

The apparatus of the invention thus comprises three essential parts:

i) means for the nerve stimulation, comprising the stimulator and the stimulus electrodes, ii) means for the detection of the muscle response, consisting of a sensor, which can be of various types, iii) means of monitoring and control, which can be of various types, depending on the specific embodiment of the invention, and iv) optionally, a closed circuit for the automatic dispensing of a drug.

The apparatus of the second embodiment can also be characterized by the fact that the means for the application of the nerve stimulation and the means for the detection of the response are arranged in a single body, whereby the advantages already described are also obtained in this instance.

Preferably, the apparatus is characterized by the fact that the body is a cuff of the type used for the measurement of arterial pressure, provided with means for the detection of the pressure or connected to said means, whose cuffincorporates means for the application of the nerve stimulation.

In this way, the electronics and the maneuvers involved in the placement of the sensor are simplified, since the same arterial pressure cuff end transducer of the noninvasive arterial pressure monitor are used. This arrangement makes it possible to simplify the technique for measurement of the neuromuscular block.

Preferably, the means for the application of the nerve stimulation comprise at least two electrodes.

Also preferably, the means for application of the nerve stimulation and the means for the detection of the pressure are combined with the means of monitoring through a multiconductor tube which contains on the inside an air conduit for transmitting the pressure waves and at least one pair of electrical conductors for transmission of the stimulation pulses.

In a preferred embodiment, said conductors are included in the wall of the multiconductor tube.

Due to the fact that there is only a single tube which transmits the pressure wave and the contraction wave and which also includes the cables with transport the stimulus, the use of the device becomes extremely simple. This solution is also more economical, since it makes use of the cuff and the electronic circuits of the arterial pressure monitor. The electrical system is more simple and less cumbersome.

The method of the invention also represents a great advance with respect to all of the foregoing ones, including the most modern (Tof-Guard and U.S. Pat. No. 5,131,401), since it does not require the stimulation of a peripheral motor nerve in order to register the muscle activity. The method of the invention is based on the stimulation of the intramuscular neural pathways and the nerve endings of the muscular motor plate by the application of a stimulus current to the skin directly over the muscle whose activity one desires to gauge.

Usually, the stimulus current does not exceed 50 mA and the time of application should not be more than 30 ms, in order not to directly stimulate the muscle fibers, which would produce a faulty reading of the neuromuscular block.

The means of monitoring can be any of the bloodless arterial pressure monitors existing on the market, modified by the incorporation of a pulse generator for the muscle stimulation, with the possibility of adjusting various parameters, such as the intensity of the stimulus or the time between readings, and with the possibility of furnishing on-screen data corresponding to the muscle relaxation.

The monitors can also have LEDs of light and sound alarm signals for cases of loss of signal or contact of the electrodes (by impedance), disconnection of the sensor or any of its parts, excessively high or low level of blockage with respect to the predetermined level, as well as other alarms which are common in medical devices, such as current faults, loss of power supply, etc.

The means of monitoring and control comprise an insulated amplifier, with filters for 50–60 Hz and high frequency to avoid interference from the electrical scalpel, a stimulator circuit of the type commonly used for nerve stimulation, capable of generating currents up to an intensity of 100 mA, a circuit to measure and control the intensity of the stimulus current, an air pump to inflate the cuff, and optionally an A/D converter, a memory bus and a microprocessor which, by means of a program in EPROM memory, controls all the functions of the device, coordinating the following closed-circuit cycle: stimulation, registration, data processing and signal processing according to standards for assessment of the neuromuscular block (evaluation of the TOF).

BRIEF DESCRIPTION OF THE DRAWINGS

In order to better comprehend what has been set forth, drawings are included which describe, schematically and only as an example, not limited hereto, the differences from the conventional methods and a practical example of realization of the stimulus-registration device, as well as the controller apparatus of the neuromuscular block.

FIG. 1 is a graph of the muscular activity, demonstrating the validity of the apparatus of the invention;

FIG. 2 is a scheme for a conventional placement of the electrodes and the sensor;

FIG. 3 is a scheme in perspective view of a pressure cuff, in which certain stimulus electrodes have been incorporated on its inner surface, with a large-scale detail of the multiconductor "tube";

FIG. 4 shows one embodiment of the apparatus of the invention; and

FIG. 5 is a flow chart of a closed circuit which controls the infusion of a muscle relaxant drug.

DESCRIPTION OF A PREFERRED EMBODIMENT

FIG. 2 shows a conventional placement of the electrodes 1, 2 and the sensor 3. In this case, the electrodes 1, 2 are arranged on the arm and the sensor 3 is arranged on the finger. One can see in the figure the two cables 4, 5 corresponding to the electrodes and the cable 6 corresponding to the sensor.

FIG. 3 shows the stimulator-detector device of the apparatus of the invention. In the figure, one can see the electrodes 7, 8 arranged in a pressure cuff 9. As the large-scale detail shows, the multiconductor tube 10 comprises an air conduit 11 and two electrical conductors 1 2 and 13. In the embodiment shown, the conductors 12 and 13 are included in the wall of the multiconductor tube 10.

FIG. 1 shows a continuous tracing curve A which corresponds to the method of the invention with the pressure cuff, provided with the stimulus electrodes arranged over the muscle in which the block is being evaluated, and a continuous tracing curve B which corresponds to a conventional method, with the stimulus electrodes over the ulnar nerve and the sensor on the thumb.

In order to demonstrate the validity of the method of the invention and to ensure that the direct cutaneous stimulation over the muscle mass in which one wishes to evaluate the neuromuscular block does not produce direct stimulation of the muscle fibers, but instead the stimulus follows the intramuscular nerve pathways and nerve endings of the muscle motor plate, the following test was performed: sensors were placed on the thumb and stimulus electrodes over the ulnar nerve, following the instructions of the previous conventional methods. Curve B was obtained.

In the same patient and at the same time, the pressure cuff with the electrodes on its inner surface was put in place, following the instructions of the method of the invention. Curve A was obtained.

Comparing the trend of both curves during the application of muscle relaxant drugs to anaesthetized patients, results were obtained which validate the method of the invention, since curves A and B show a similar behavior for the same method of application of the drugs.

FIG. 4 shows the different components of the apparatus of the invention:

In the first place, the stimulator-detector device 14 detailed in FIG. 3, which includes the stimulus electrodes 7, 8 and the pressure cuff 9. This can be made in different sizes, depending on the size of the limb to which it is applied, it being possible to have versions for adults and versions for children.

The device can be disposable or reusable, and it comprises the two electrodes 7, 8, likewise disposable or reusable, which are coupled to the cuff and have a stimulus surface varying between 0.05 cm2 to 5 cm2 for each. The electrodes 7, 8 are placed on the inner surface of the arterial pressure cuff 9, which, with the muscle contraction wave transmitted to the skin, generates a pressure wave proportional to the muscle contraction that is transmitted through the tube to the pressure transducer, arranged inside a conventional type of arterial pressure monitor 15.

The stimulation electrodes 7, 8 can be situated in various ways on the inner surface of the cuff 9. The more far apart they are, the greater the number of nerve endings stimulated and the larger will be the response.

The cycle used for the measurement is as follows:

1) Inflate the cuff slightly to ensure good contact between the electrodes and the skin (between 10 and 300 mmHg).
2) Generation and application through cutaneous electrodes of a series of four stimuli <50 mA and <30 me in duration at a frequency of 2 Hz, known as "TOF" ("Train of Four", the standard accepted in all methods of evaluation of the neuromuscular block).
3) Registration of the pressure generated inside the cuff by the wave which is transmitted to the surface of the skin by the contractions of the muscle.
4) Digitization and processing of the signal, graphic representation through an LCD or electroluminescent screen.

FIG. 4 shows one embodiment of the apparatus of the invention. In this figure, one can see the stimulator-detector device 14 as represented in FIG. 3 and a conventional type of arterial pressure monitor 15.

In the lower righthand portion of the monitor dial 15 one can see the connections 16, 17 and 18, corresponding respectively to the multiconductor tube 10, the information on oxygen saturation, and the electrocardiogram.

In the upper righthand portion one can see a pair of control buttons, one of which 19 serves to adjust the time between two readings and the other 20 is used to adjust the intensity of the stimulus.

On the screen at left there appear two curves, the upper one corresponding to the electrocardiogram and the lower one to the pulse signal or plethysmogram. The bars in the lower part of the screen represent the responses to the muscular stimulation over time. The screen can also display data such as the muscular activity (Musc: 30%), heart rate (FC: 60), arterial pressure (PA: 120/70), and oxygen saturation (Sat: 98%).

The conventional monitor 15 is provided with a pulse generator for the muscle stimulation through the conductors 12, 13 (FIG. 3) and the electrodes 7, 8.

FIG. 5 shows a flow chart of a closed circuit. The electrical stimulator 21 stimulates the muscle 22. The sensor 23 provides the muscle response to the means of control 24.

A program is used to control the data acquisition, A/D conversion, and analysis of the data, furnishing the signals to actuate the system for supply or infusion of the muscle relaxant 25. In this way, the infusion will be automatic.

I claim:

1. A method of monitoring neuromuscular block and particularly that produced by muscle relaxant drugs used during anesthesia, the method comprising the steps of, stimulating the skin covering the muscle in which the detection of the response to the stimulation is performed and without stimulating any peripheral nerve, detecting the muscle response to said stimulation, and measuring said response.

2. The method set forth in claim 1 including the step of controlling the supply of muscle relaxant to the patient in relation to the detected muscle response.

3. The method set forth in claim 1 wherein said method is performed using a pressure cuff and a nerve stimulator and sensor are mounted in the cuff, comprising the further steps of applying the pressure cuff to the patient's skin at a point covering the muscle to be stimulated, pressurizing the cuff to position the electrode against the skin, and applying a stimulating signal to the electrode.

4. The method set forth in claim 3 including the step of sensing changes in the pressure within the cuff as an indication of muscle response.

5. An apparatus for monitoring neuromuscular block, particularly the block produced by muscle relaxant drugs during anesthesia, said apparatus comprising a pressure cuff, first means disposed on the pressure cuff for applying nerve stimulation to the skin covering the muscle on which detection of the response of the stimulation is to be performed, and second means disposed on said pressure cuff for detecting the response to the stimulation, and means for monitoring the neuromuscular block.

6. An apparatus for monitoring neuromuscular block, and particularly the block produced by muscle relaxant drugs during anesthesia,
    said apparatus including a nerve stimulator constructed and arranged to apply nerve stimulation to the skin covering the muscle on which the detection of the response to the stimulation is performed and without the necessity of stimulating any peripheral nerves,
    a detector constructed and arranged to detect the response to the stimulation, a monitor constructed and arranged to monitor the neuromuscular block,
    a drug supplier constructed and arranged to supply the drug which produces the neuromuscular block,
    and a processor programmed to coordinate the generation of the stimulants, to register the activity as a result of the stimulus, to compute the drug dosage and to control the means for supplying the drug supplied as a function of the computed dosage.

7. The apparatus set forth in claims 6 and including an arterial pressure measurement cuff, said nerve stimulator being mounted on the pressure cuff said detector being constructed and arranged to detect the pressure within said cuff.

8. The apparatus set forth in claim 7 and including a body, said means for the application of nerve stimulation and the means for detecting a response to the nerve stimulation are disposed on said body.

9. The apparatus set forth in claims 5 or 8 wherein said body is an arterial pressure measurement cuff, said means for detecting the response to the stimulation comprising means for detecting the pressure within said cuff.

10. The apparatus set forth in claims 5 or 8 wherein the means for the application of nerve stimulation comprises at least two electrodes.

11. The apparatus set forth in claim 9 and including a monitor, a conduit connecting the monitor to the pressure cuff for transmitting pressure waves, and electrical conductor means extending through the conduit and coupled to the means for the application of nerve stimulation.

12. The apparatus set forth in claim 11 wherein the conduit has a wall, said conductors being mounted in the wall of the conduit.

13. The apparatus set forth in claims 5 or 8 wherein the means for the application of nerve stimulation comprises a pressure cuff having at least one electrode positioned to engage the skin when the cuff is applied.

14. The apparatus set forth in claim 13 wherein the means for monitoring the neuromuscular block comprises means for sensing pressure changes in the cuff.

15. The apparatus set forth in claims 6 wherein said body is an arterial pressure measurement cuff, and a detector constructed and arranged to detect the pressure within said cuff.

16. An apparatus for monitoring neuromuscular block, particularly the block produced by muscle relaxant drugs during anesthesia, said apparatus comprising a body, a nerve stimulator mounted on the body for applying nerve stimulation to the skin covering the muscle on which detection of the response of the stimulation is to be performed, and a detector mounted on said body for detecting the response to the stimulation, and a monitor for monitoring the neuromuscular block.

17. The apparatus set forth in claims 16 or 15 wherein the nerve stimulator comprises at least two electrodes.

18. The apparatus set forth in claim 15 and including a conduit connecting the monitor to the pressure cuff for transmitting pressure waves, and an electrical conductor extending through the conduit and coupled to the means for the application of nerve stimulation.

* * * * *